United States Patent [19]

Rhodes et al.

[11] 4,416,865

[45] Nov. 22, 1983

[54] RADIOPHARMACEUTICALS FOR LOCALIZATION OF THROMBOEMBOLIC DISEASE

[75] Inventors: Buck A. Rhodes; William R. Bell, both of Baltimore, Md.

[73] Assignee: Research Corporation, New York, N.Y.

[21] Appl. No.: 333,802

[22] Filed: Feb. 20, 1973

[51] Int. Cl.³ .................... A61K 49/00; A61K 43/00
[52] U.S. Cl. .................................. 924/1.1; 424/1.5; 424/9
[58] Field of Search ................................. 424/1, 9

[56] References Cited

U.S. PATENT DOCUMENTS

| | | | |
|---|---|---|---|
| 3,636,201 | 1/1972 | Johnson | 424/1 |
| 3,740,418 | 6/1973 | Rajamani et al. | 424/1 |
| 3,812,245 | 5/1974 | Dugan | 424/1 |

OTHER PUBLICATIONS

Bogolyubov, Nuclear Science Abstracts, vol. 21, No. 20, Oct. 31, 1967, p. 3834, #36623.

*Primary Examiner*—Christine M. Nucker
*Attorney, Agent, or Firm*—Scully, Scott, Murphy & Presser

[57] ABSTRACT

The invention relates to radiopharmaceuticals useful for specifically localizing blood clots during the diagnosis and treatment of thromboembolic disorders. In one embodiment, the invention comprises a method for preparing and using radioactive urokinase. A novel process for producing urokinase labeled with technetium-99m involves combination of urokinase with the nuclide in a basic solution containing ferric chloride and ascorbic acid, and then adjusting the pH to give an acidic condition in the solution. Radioactively-labeled streptokinase and fibrinokinase are also used to localize thromboembolic disorders.

14 Claims, 13 Drawing Figures

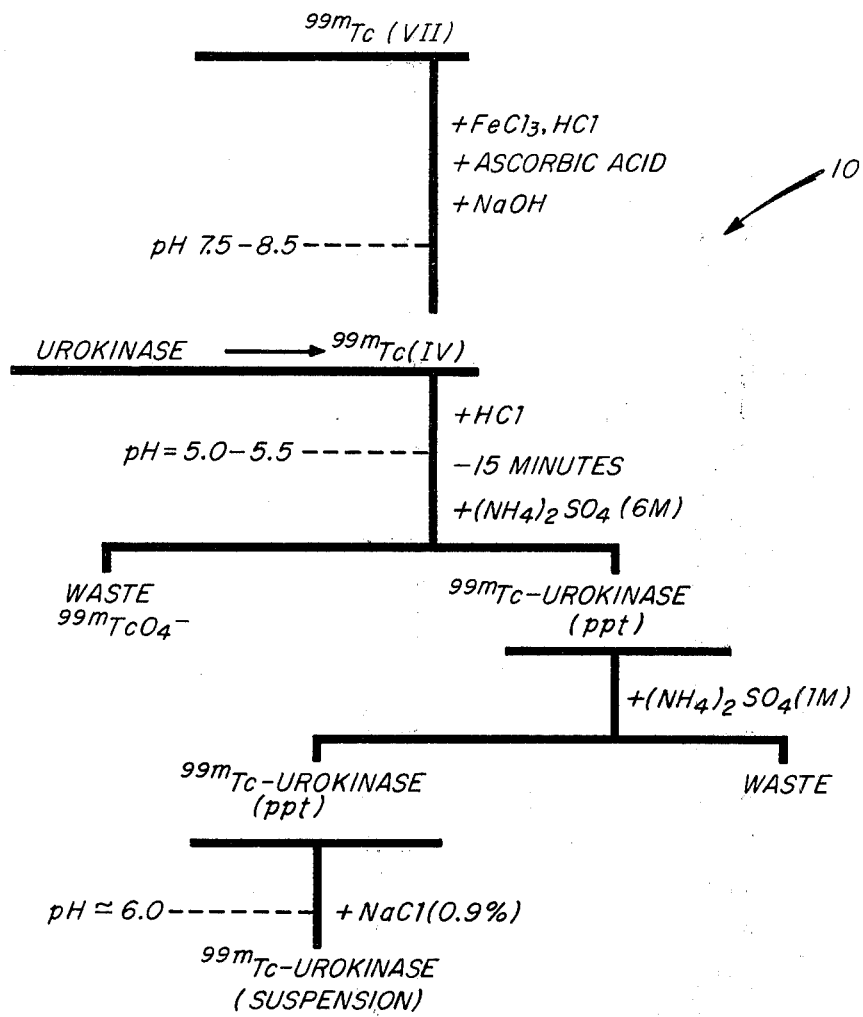
FIG. 1
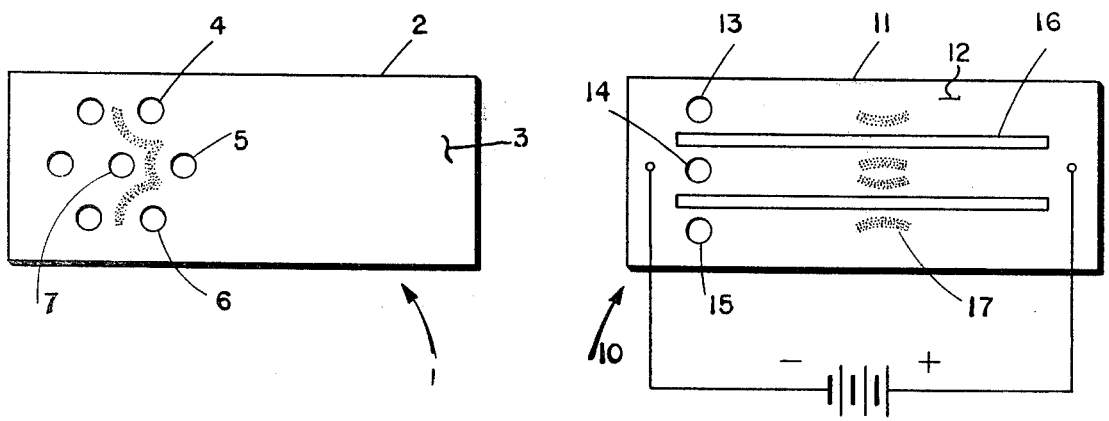
FIG. 3
FIG. 4

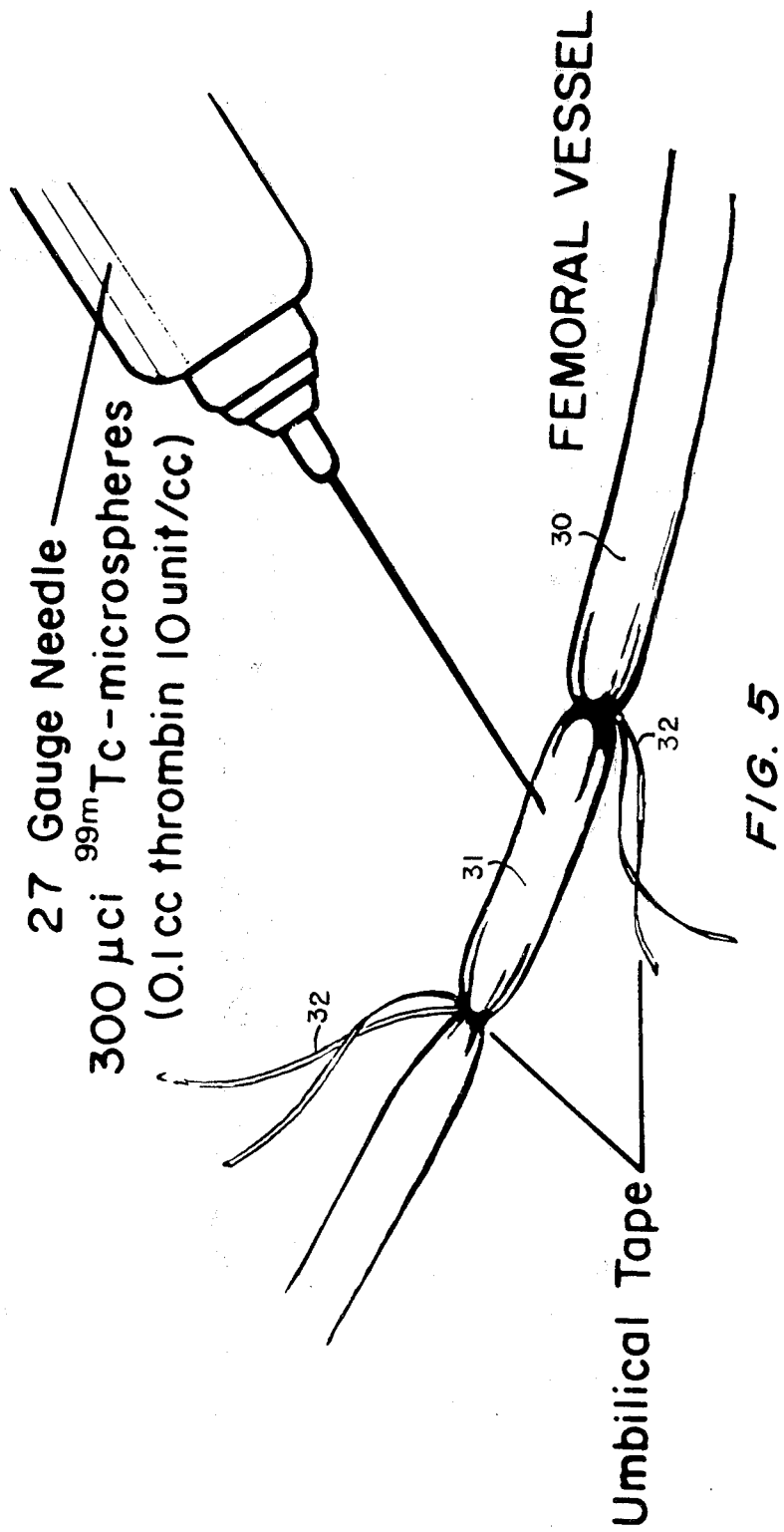

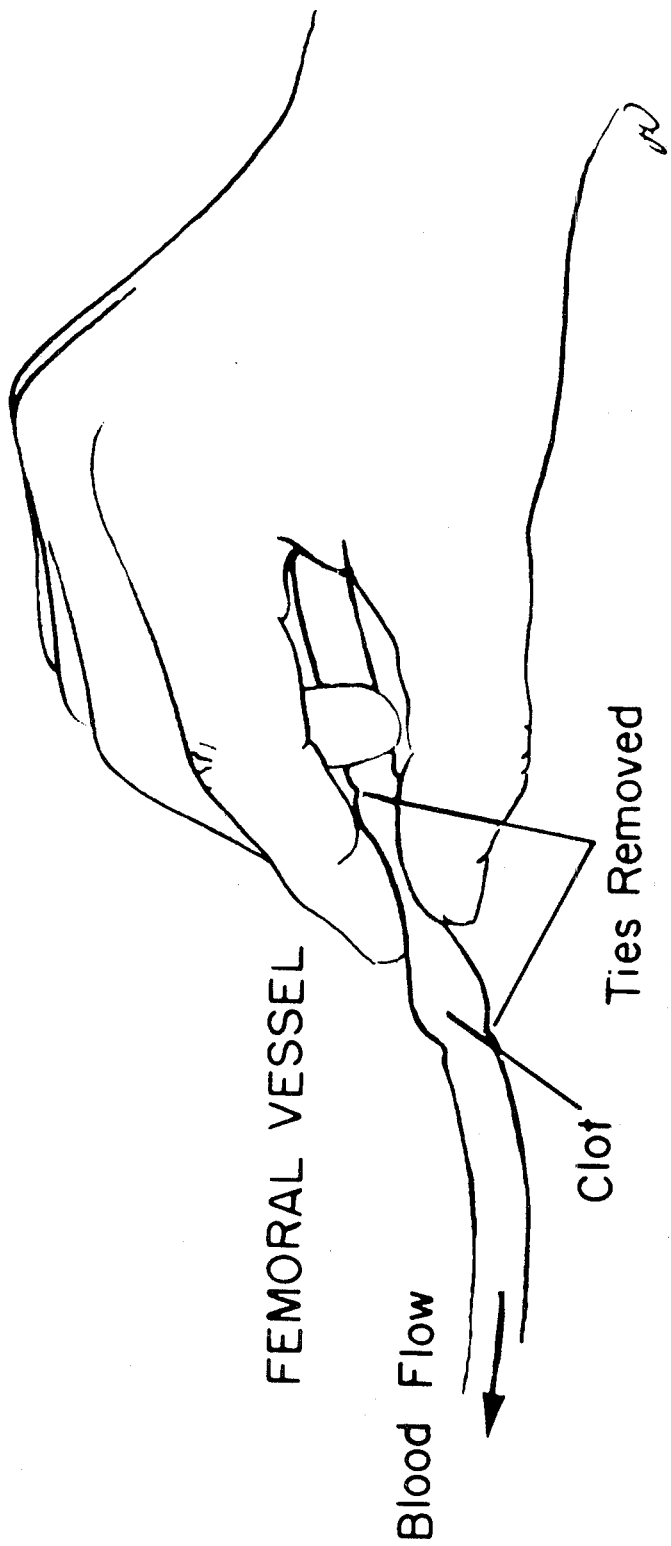

RADIOPHARMACEUTICALS FOR LOCALIZATION OF THROMBOEMBOLIC DISEASE

STATEMENT OF GOVERNMENT INTEREST

The invention described herein was made in the course of work under a grant or award from the Department of Health, Education, and Welfare.

BACKGROUND OF THE INVENTION

A. Field of the Invention

The invention relates primarily to compositions of matter and process for preparation thereof, the compositions of matter comprising an enzyme labeled with a radioactive nuclide. The resulting radioisotope is specifically absorbed by blood clots, thereby providing a method for localizing thromboembolic disorders.

B. Description of the Prior Art

The use of radionuclides as medical diagnostic tools has increased in recent years. As an example, technetium-99m labeled organic chelates, such as are disclosed by Richards et al in U.S. Pat. No. 3,466,361, have been used for scintophotographic scanning in brain tumor localization, thyroid visualization, etc. Technetium-99m exhibits characteristics which render it a desirable radionuclide for medical applications due to a combination of advantageous physical characteristics. Since this radionuclide has a six hour half-life and does not emit beta radiation, millicurie amounts of the substance may be administered to a patient with only minimum radioactivity dosages. The gamma emission of 140 Kev. satisfactorily penetrates tissue while being readily collimated for ease of use with most scanning equipment. A substance containing technetium-99m which clears the blood readily, does not enter metabolic processes, and specifically localizes blood clots would thus be of great benefit in the diagnosis and treatment of thromboembolic disease. Several substances have been proposed in the art for such a use, among them fibrinogen, antifibrin, technetium-labeled platelets, and various radioactive particles. The present invention provides inter alia radioactive urokinase, one form of which is labeled with technetium-99m, for specifically localizing blood clots associated with thromboembolic disease. The present compounds exhibit advantages over those substances previously proposed since they are less likely to be antigenetic; they clear the blood stream rapidly; they do not have to be injected prior to clot formation; they are stable; and they can be purified readily and separated from lingering contaminants such as hepatitis virus.

SUMMARY OF THE INVENTION

The invention described herein was made in the course of, or under U.S. Public Health Service Grant GM 10548.

The present invention provides radioactive enzymes, a process for preparing at least one of the enzymes, and a process for use of the enzymes and other compounds wherein blood clots associates with thromboembolic disease are detected, located, and treated. Three of the present compounds are formed from an enzyme, urokinase, which has been reacted with a radionuclide, such as technetium-99m, $^{131}$I or $^{123}$I to produce the first radiopharmaceuticals which are specific for thromboembolic disease. The process for preparing the technetium-labeled compound involves: (a) reacting technetium-99m with ferric chloride and ascorbic acid in a solution made acid by the addition of hydrochloric acid; (b) rendering the solution basic through the addition of sodium hydroxide; (c) adding urokinase to the solution; and, (d) adjusting the pH of the solution by adding hydrochloric acid to render the solution acidic. The $^{99m}$Tc-urokinase thus formed is separated from the reaction mixture by precipitating the substance from solution with ammonium sulfate. Urokinase labeled with $^{131}$I may be formed using the well-known chloramine-T method.

The radiopharmaceuticals of the invention are typically used in the treatment of suspected thermoembolic disease by having the radiopharmaceutical injected into a vein and having the patient scanned with a rectilinear scanner or other well-known device to produce an image of the distribution of the radioactivity in the patient's body. Since blood clots specifically absorb the present substances, an area of localized radioactivity indicates a blood clot formation, thereby confirming the presence of a thromboembolic disorder. The patient is then further treated with anticoagulants or with enzymes to dissolve the clots. Since treatment with anticoagulants can cause spontaneous bleeding and hemorrhage, it is imperative that definitive evidence of thromboembolic disease be found before initiating such treatment. Prior to the present invention, symptomatic evidence of thromboembolic disease was usually the only basis for further treatment. The specific indication for thromboembolic disease provided by the present invention will prevent unnecessary treatment and hospitalization which may sometimes occur when the patient's symptomatic responses are caused by conditions other than thromboembolic disease.

It is therefore an object of the invention to provide enzymatic substances labeled with radionuclides which are specific for localizing thromboembolic diseases in the human body.

It is a further object of the invention to provide a method for preparing $^{99m}$Tc-urokinase, an enzyme labeled with technetium-99m and which is specific as a radioactive tracer for thromboembolic disease due to absorption thereof by blood clot formations in the body.

It is another object of the invention to provide a process for localizing thromboembolic disease in the body through the use of specific radionuclide-labeled enzymatic substances.

Further objects and advantages of the invention will become more apparent in light of the following detailed discussion of the invention.

BRIEF DESCRIPTION OF THE DRAWINGS

FIG. 1 is a schematic illustrating the sequence of steps required to prepare $^{99m}$Tc-urokinase according to the present invention;

FIG. 3 is a plan view of a gel diffusion slide with which the chemical properties of radionuclide-labeled urokinase have been compared to the properties of unlabeled urokinase;

FIG. 4 is a plan view of a gel-electrophoresis slide with which the chemical properties of radionuclide-labeled urokinase have been compared to the properties of unlabeled urokinase;

FIG. 5 is an idealized perspective view illustrating a first step of a method for preparing a thromboembolus in a femoral vessel;

FIG. 6 is an idealized perspective view illustrating a second step of the same method that is treated in FIG. 5;

DESCRIPTION OF THE PREFERRED EMBODIMENTS

Figure 2:
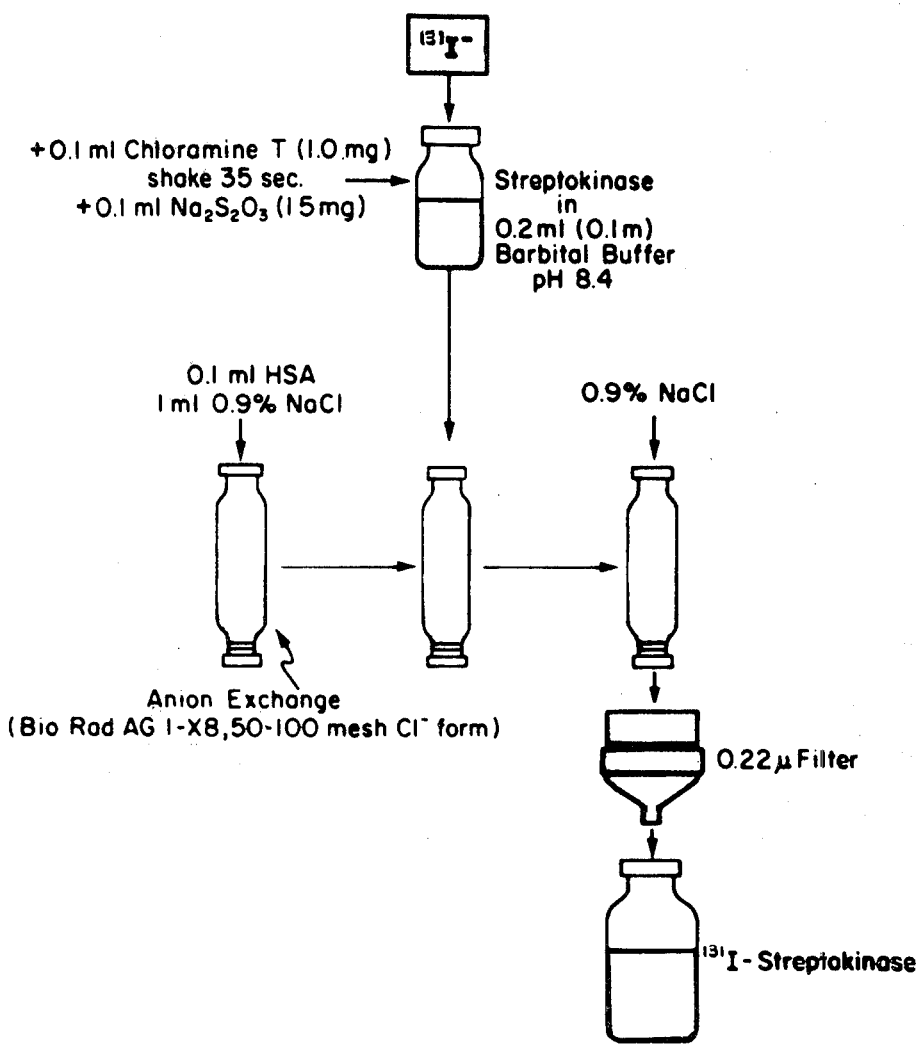
FIG. 2 is a diagram which illustrates the sequence of steps necessary for preparing streptokinase labeled with the radionuclide, $^{131}$I.

A native human protein, urokinase, may be reacted with the radionuclides $^{99m}$Tc, $^{131}$I and $^{123}$I to produce a labeled radiopharmaceutical which retains enzymatic activity and localizes blood clots in vivo, thereby providing specific diagnosis for thromboembolic disease. Referring to FIG. 1, a method for preparing the technetium-99m labeled enzyme is shown in flow chart form. Radioactive technetium-99m may be prepared by any known method which yields a high purity radionuclide, such as is described by Arino in U.S. Pat. No. 3,468,808. A saline solution containing from one to five millicuries of technetium-99m has an excess of ferric chloride added thereto in order to completely reduce the technetium-99m. The solution is maintained in an acidic condition with hydrochloric acid. Ascorbic acid is then added to the solution and the pH adjusted to between 7.5 and 8.5 with sodium hydroxide. The technetium-99m is now in a chemical state wherein reaction with urokinase will occur. Urokinase of 20,000–100,000 CTU's in 0.2 cc of saline is added to the solution containing the technetium-99m, the pH of the total solution is adjusted with hydrochloic acid to between 5.0 and 5.5 and the reaction mixture is allowed to stand under standard conditions for fifteen minutes. The $^{99m}$Tc-urokinase thus formed is precipitated from solution by adding 3–5 milliliters of saturated ammonium sulfate. Centrifugation at 2,000 rpm for ten minutes and decantation of the supernatant liquid covering the labeled urokinase yields the desired product. The labeled urokinase is then washed in the 1.0 M ammonium sulfate and then dissolved in 0.9% saline and passed through a 0.45-micron Millipore filter to further purify the product.

FIGS. 3 and 4 illustrate experiments which indicate that the chemical activity of the urokinase labeled with $^{131}$I and technetium-99m does not differ from the unbound urokinase. FIG. 3 shows at 1 a gel diffusion slide which comprises a glass plate 2 having a film 3 of agar disposed thereon. Receiving wells 4, 5, 6, and 7 are formed in the agar film 3. $^{131}$I-urokinase, unbound urokinase, $^{99m}$Tc-urokinase, and sera obtained from a donor made allergic to urokinase are then respectively placed one each in the wells, 4, 5, 6, and 7. These substances each diffuse radially through the agar film 3 at a rate dependent on the chemical activities thereof and meet along arc-like lines in the agar film. The sera contains antibody molecules which typically react with unbound urokinase to form a precipitate capable of forming a dark line in the agar film. As seen in the drawing, a series of intersecting dark, arc-like lines 8 are formed in the film 3. The position and presence of the lines 8 show that the diffusion rates of the two radionuclide labeled urokinase compounds is essentially the same as that of the unbound urokinase and the reactivity to antibody-containing sera is also essentially the same. Therefore, the chemical activity of the labeled urokinase compounds is the same as that of unbound urokinase. Further proof of maintenance of normal chemical activity in the radionuclide labeled urokinase compounds may be seen by referring to FIG. 4. A gel-electrophoresis slide 10 is seen to comprise a glass plate 11 covered by an agar gel film 12. Receiving walls 13, 14, and 15 are formed in the film 12 and $^{131}$I-urokinase, unbound urokinase, and $^{99m}$Tc-urokinase are respectively added one each to said wells. Slots 16 containing sera from a donor made allergic to urokinase are disposed longitudinally in the slide 10. Prior to placing the antibody-containing sera in the slots 16, a voltage is applied across the slide 10, thereby causing the substances in the wells 13, 14, and 15 to migrate therefrom to positions along the slide which depend on the nature of the substances. The voltage is then removed prior to placing the antibody-containing sera in the slots 16. The sera then diffuses from the slots 16 into contact with the substances which have migrated from the wells 13, 14, and 15 and reacts with said substances as was described relative to FIG. 3 to form the curved lines 17. The location and presence of the lines 17 indicate that substances of substantially the same chemical activity were originally placed in the wells 13, 14, and 15. Thus, the radionuclide labeled urokinase compounds retain the chemical behavior of unbound urokinase.

Figure 12:
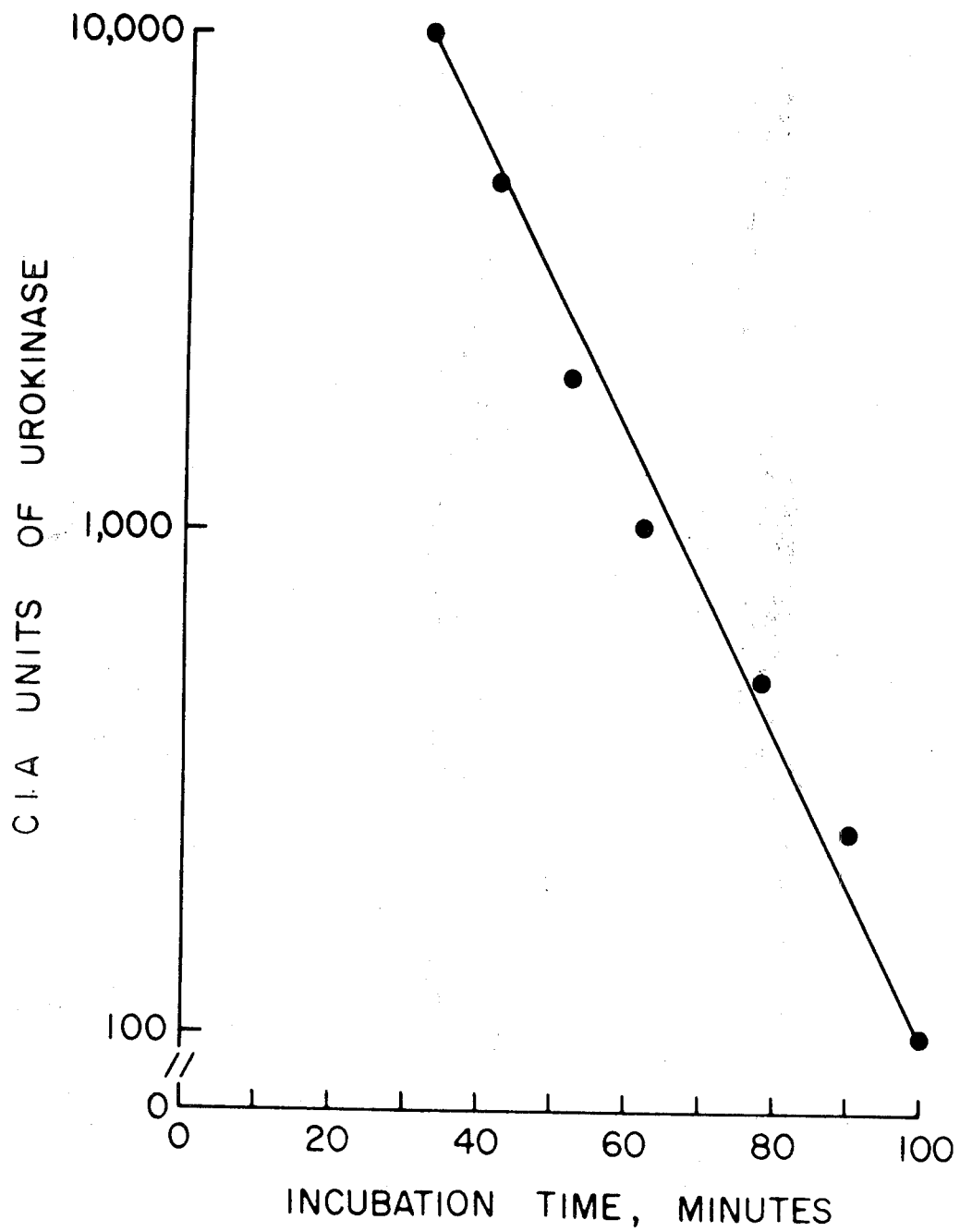
FIG. 12 is a graph illustrating the standard curve for urokinase enzymatic activity determination.

The enzymatic activity of the $^{131}$I-urokinase and $^{99m}$Tc-urokinase is determined by measuring the time required by the labeled compound to lyse fibrin clots. Referring to FIG. 12, of lysis times of urokinase dilutions in the range of 100 to 10,000 CTU's result in a straight line calibration curve when semi-logarithmically plotted against enzyme activity. Fibrin clots used in obtaining the information revealed in the graph were prepared by mixing 0.1 ml of 0.9% saline containing one unit of thrombin of bovine origin with 0.1 ml of 1% bovine fibrinogen in 0.9% saline. The clots were aged one hour at 4° C. then warmed to 37° C. by incubation in a waterbath. The urokinase to be tested along with the dilutions of the standards was added in 0.1-ml volume to the clots. Barbitol buffer (0.4 ml) of pH 7.6 was also added. The times required for lysis was recorded to obtain the information shown in FIG. 12. Based on the standard curve of FIG. 12, the radionuclide labeled urokinase compounds retain 70 to 100% of enzymatic activity. Incubation of the labeled enzymes at room temperature for one-half hour in solutions of pH ranging from 2.5 to 10.0 did not diminish the enzymatic activity nor did passing the materials through a 0.22 micron Millipore filter.

Figure 10:
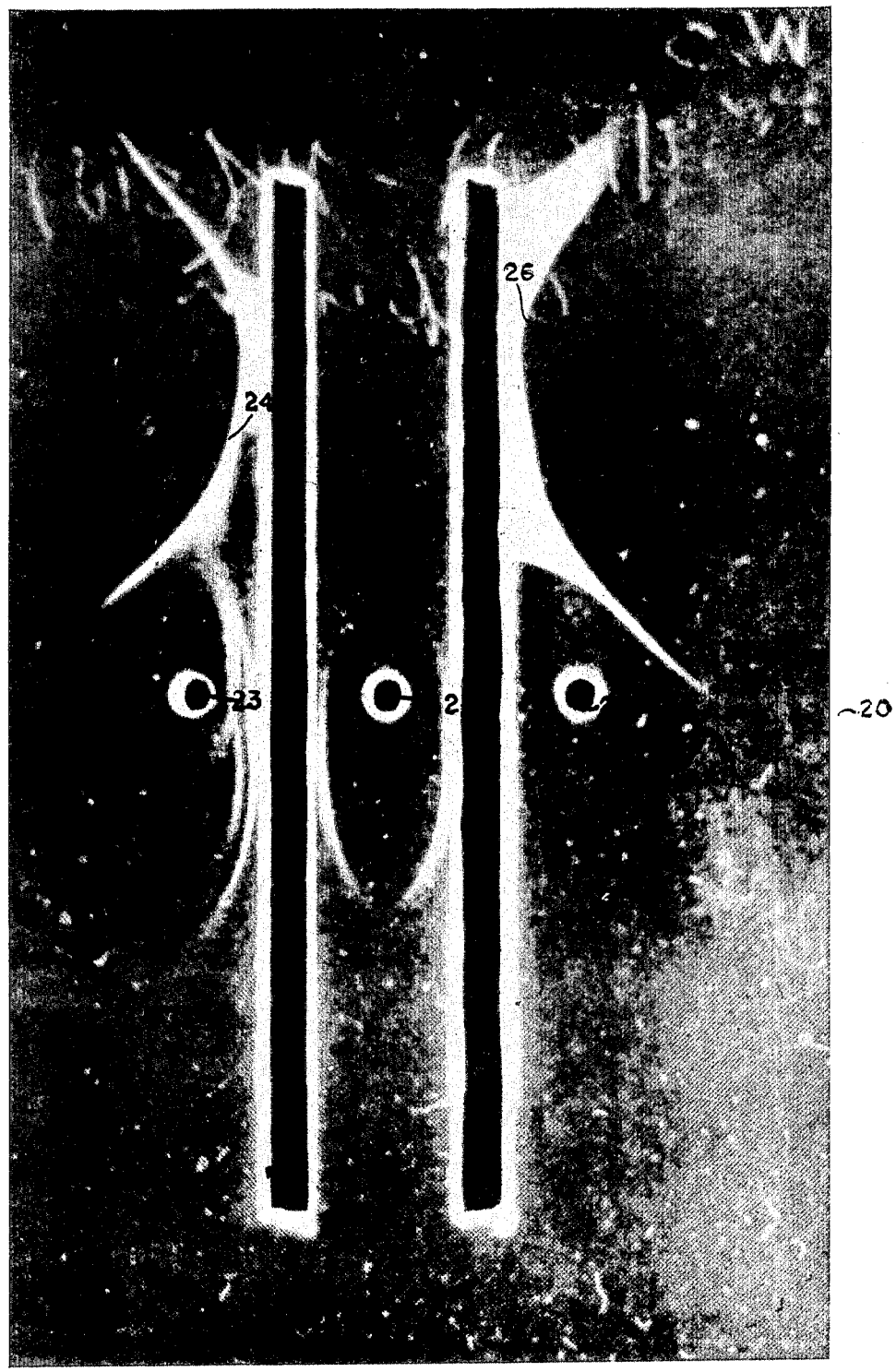
FIG. 10 is an immunoelectrophoretic slide illustrating an analysis of the enzymatic activity of $^{99m}$Tc-urokinase prepared from urokinase obtained from different sources.
Figure 11:
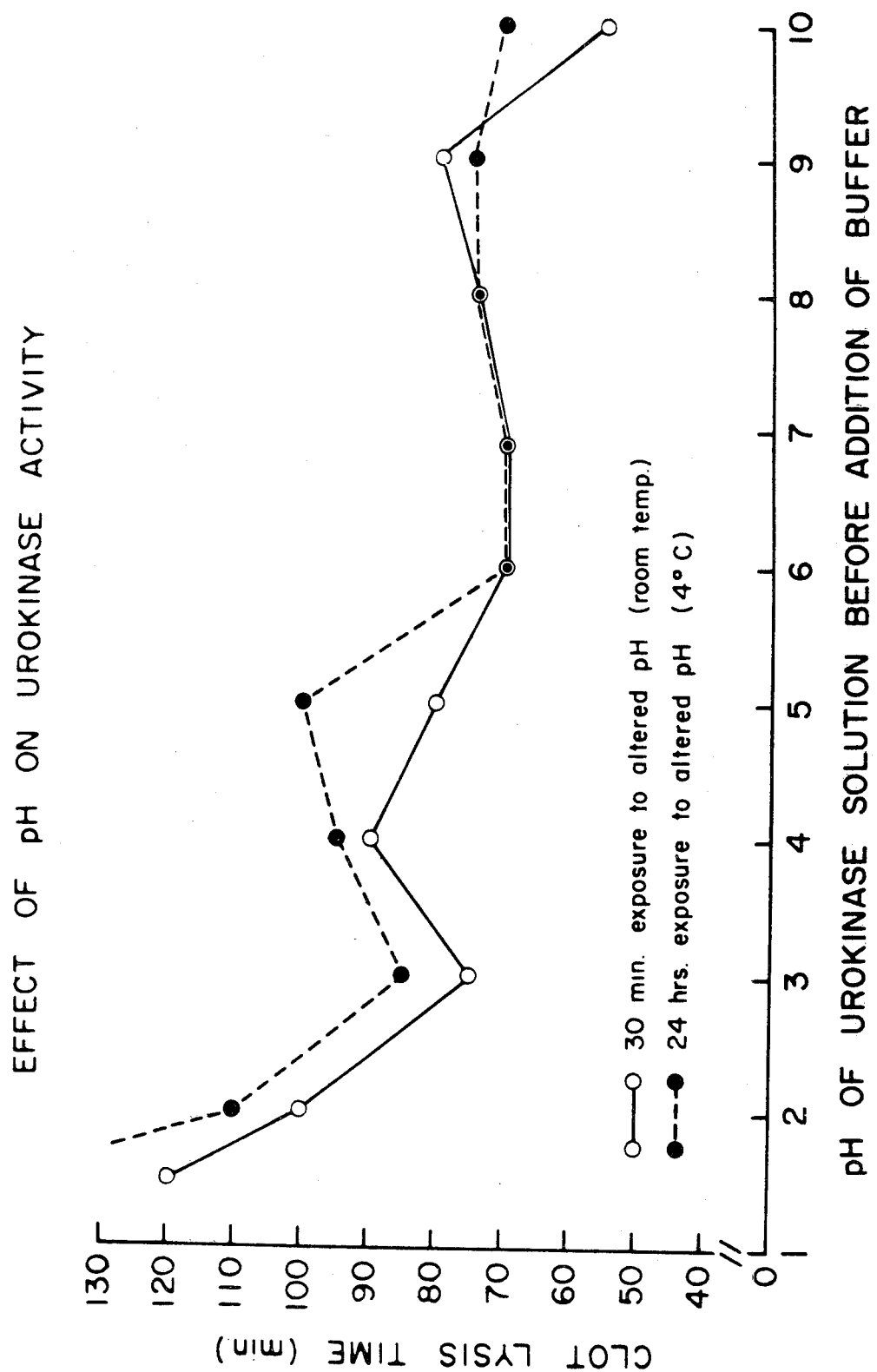
FIG. 11 is a graph illustrating the effect of pH on urokinase activity.

Since the urokinase used to prepare the present compounds must be relatively free from human serum albumin, urokinase is obtained from the Sterling Winthrope Company. FIG. 10 shows an immunoelectrophoresis slide 20 similar to that shown in FIG. 4. The slide 20 has wells 21, 22, and 23 which respectively contain Abbott Laboratories urokinase, Sterling Winthrope urokinase and human serum albumin. After electrophoresis, the lines 24 were developed with antibody-containing serums, i.e., the IgG fraction of whole rabbit serum, and show that the urokinase in well 21 has multiple protein components while the urokinase in well 22 has only two components. Use of the urokinase which was placed in well 21 to prepare radionuclide labeled urokinase would result in heavy concentration of the radionuclide in the albumin fraction of the material.

A third compound which has been found to be of use in the diagnosis of thromboembolic disease in the enzyme streptokinase labeled with the radionuclide $^{131}I$. Although the radionuclide-labeled urokinase compounds disclosed hereinabove have certain advantages over streptokinase, such as being less antigenetic than streptokinase since urokinase is a native human protein, labeled streptokinase may be used in instances where urokinase is not suitable due to patient reaction. Preparation of $^{131}I$-streptokinase is illustrated in FIG. 2, the radionuclide $^{131}I$ being obtained as Na $^{131}I$ in 0.1 M sodium hydroxide in a concentration of 50 mCi/ml. As seen in FIG. 2, 0.2 ml of 0.1 M barbital buffer (pH 8.4); 0.2 ml of 9% NaCl; 100,000 units of Hoechst streptokinase (60,000 units/mg, 500,000 units/ml); and 5 mCi of $^{131}I$ are mixed together with one hundred microliters of chloramine-T and allowed to react for thirty-five seconds, after which 100 microliters of disodium thiosulfate is added to terminate the reaction. The pH of the reaction mixture should be maintained above 8.0 and an excess of chlormaine-T should be present to reduce reaction time and minimize damage to the protein. The $^{131}I$-streptokinase is separated from the reaction mixture using known procedures such as are described hereinabove. Sterilization is accomplished by filtration through a suitable Millipore filter.

Figures 9, 9A, 9B:
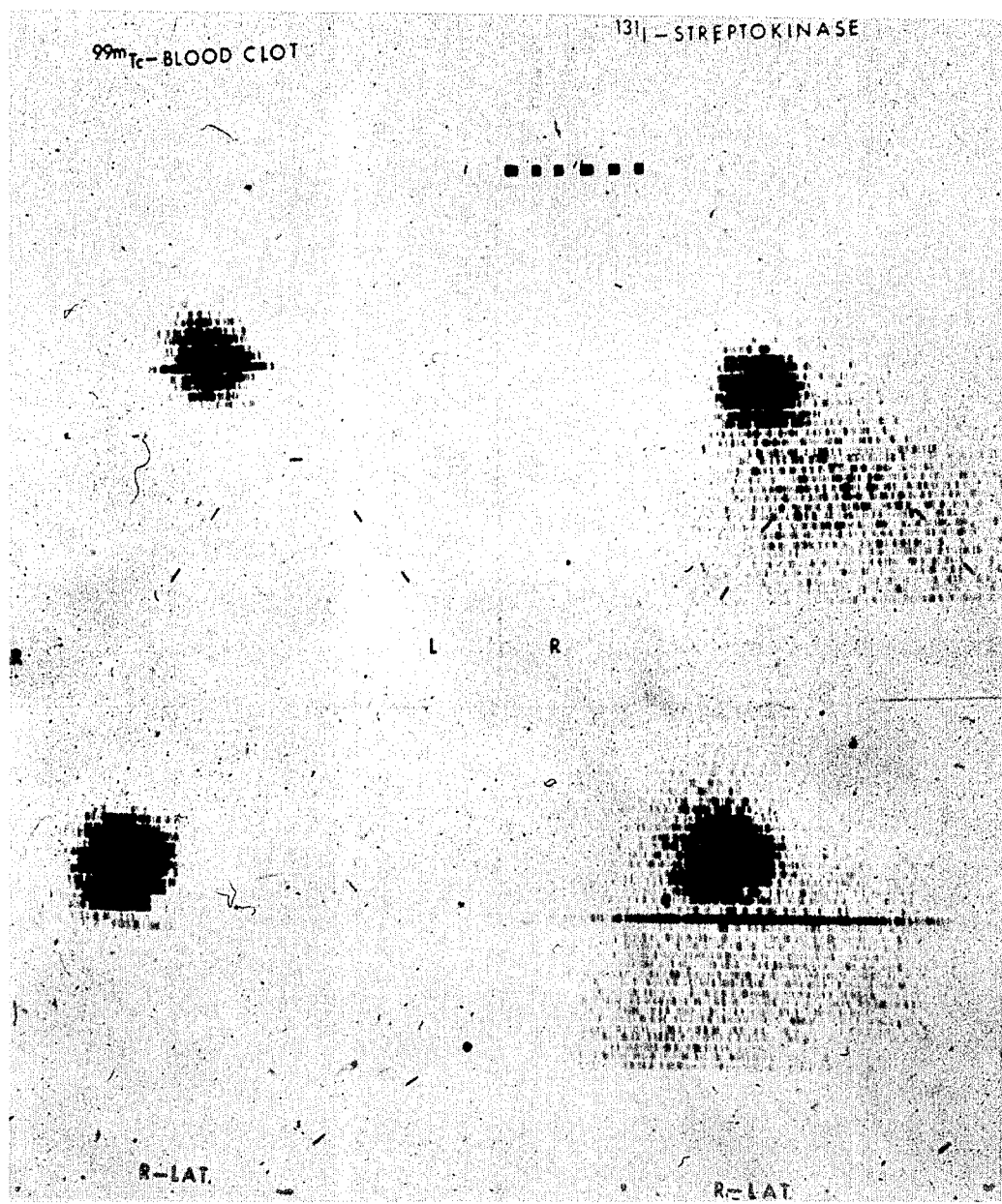
FIG. 9a is a lung scan depicting $^{99m}$Tc activity in a $^{99m}$Tc-labeled clot in a lung.
FIG. 9b is a lung scan depicting $^{131}$I activity in the same lung as was viewed in FIG. 9a but one hour after injection with $^{131}$I-streptokinase.

FIGS. 5 and 6 illustrate a method for preparing thromboemboli in vivo in order to confirm localization of blood clots by use of the present radionuclide-labeled substances. A femoral artery or vein 30 of a suitable test animal is surgically exposed and stasis is induced in a 2.0 cm segment 31 by ligating the vessel proximally and distally with umbilical tape 32. An injection of 0.1 ml (10 units/ml) of Parke-Davis Thrombin-Topical (bovine origin) and 300 microcuries (0.1 ml) of $^{99m}Tc$-microspheres is made into the ligated segment 31 and the segment is incubated for ten to fifteen minutes. The tape 32 is then removed and the thromboemboli thus formed are "milked" as shown in FIG. 6 by digital compression to cause embolization in the direction of blood flow. The chest and extremities of the test animal is then scanned for emboli using well-known apparatus, such as a Picker rectilinear scanner, to determine the location in the body of the animal in which the thromboemboli have settled. Such a scan is shown in FIG. 9a.

Thirty minutes after the steps described, an injection of $^{131}I$-urokinase or $^{131}I$-streptokinase, is made into a non-traumatized extremity. Serial scans, such as the one shown in FIG. 9b, are then made at time intervals of 15, 60, and 120 minutes over the same areas where thromboemboli had been previously detected, the scanning device being adjusted to exclude $^{99m}Tc$ activity. In the scans thus made, visually perceptible increases in radioactivity are evident over the same areas where the $^{99m}Tc$-microspheres had indicated emboli. Thus, the absorption of the iodinated urokinase and streptokinase by a blood clot in vivo is shown and proves adequate for localization of thromboembolic disease.

Figure 7:
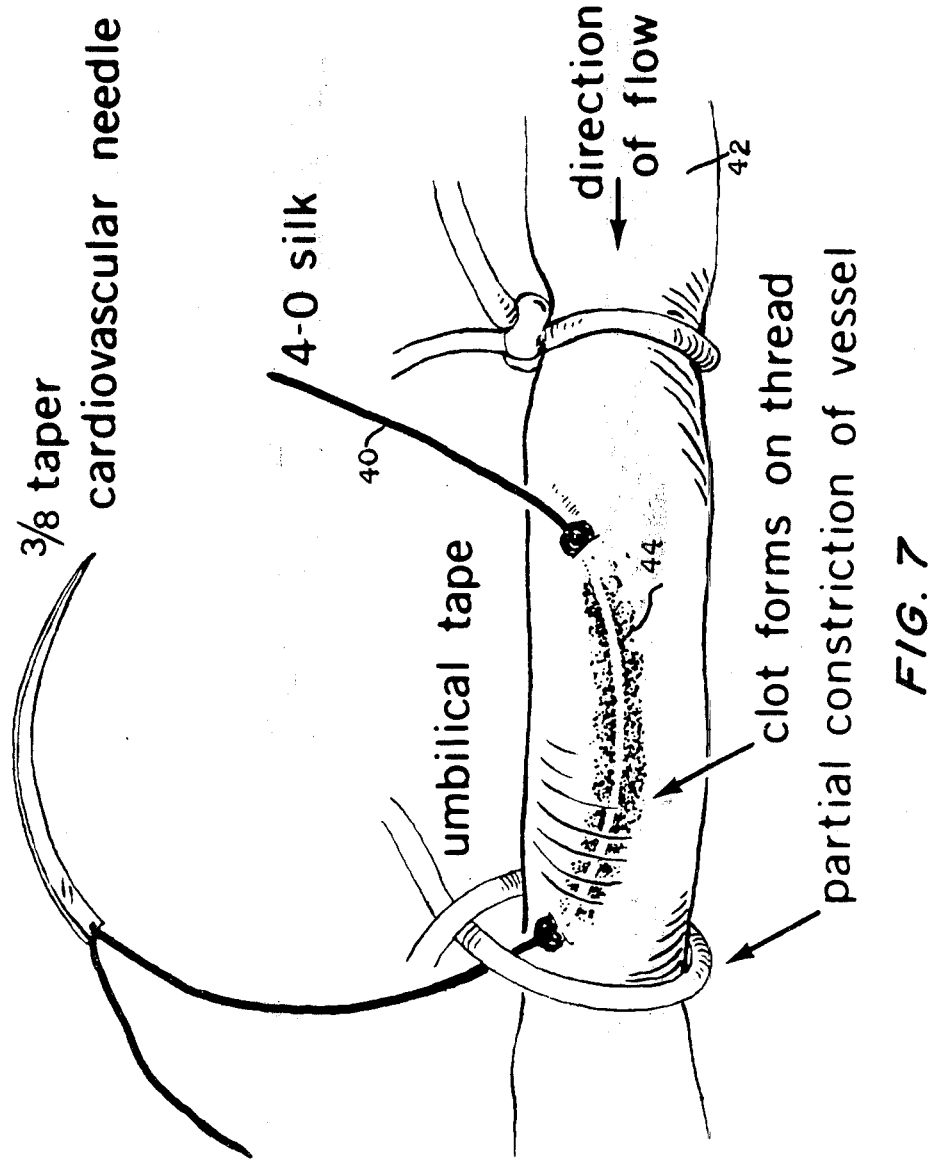
FIG. 7 is an idealized perspective view illustrating a method for preparing retrievable clots in vivo.

FIG. 7 illustrates a method for determining the in vivo concentration of $^{131}I$-urokinase, $^{99m}Tc$-urokinase, or $^{131}I$-streptokinase in blood clots. A 4-0 silk suture 40 is soaked in thrombi and sewn into the lumens of a partially constricted femoral artery or vein 42 of a suitable test animal. One to three hours later, one of the radiopharmaceuticals of the present invention is given intravenously in another extremity, the clots 44 which had previously formed on the suture 40 being removed by dissection two to four hours after injection of the labeled enzyme. The clots 44 which form on the suture 40 are isolated, dried in air, and weighed. Blood samples obtained at the same time are similarly isolated, dried, and weighed. The concentration of radioactivity in the clots 44 is significantly higher than the concentration of radioactivity in the blood. Thus, the clots 44 absorb and retain the labeled enzymes while most of the unabsorbed enzyme is cleared from the bloodstream through the kidneys. The present compounds are thus shown to be useful for localizing blood clots associated with thromboembolic disease.

Figure 8:
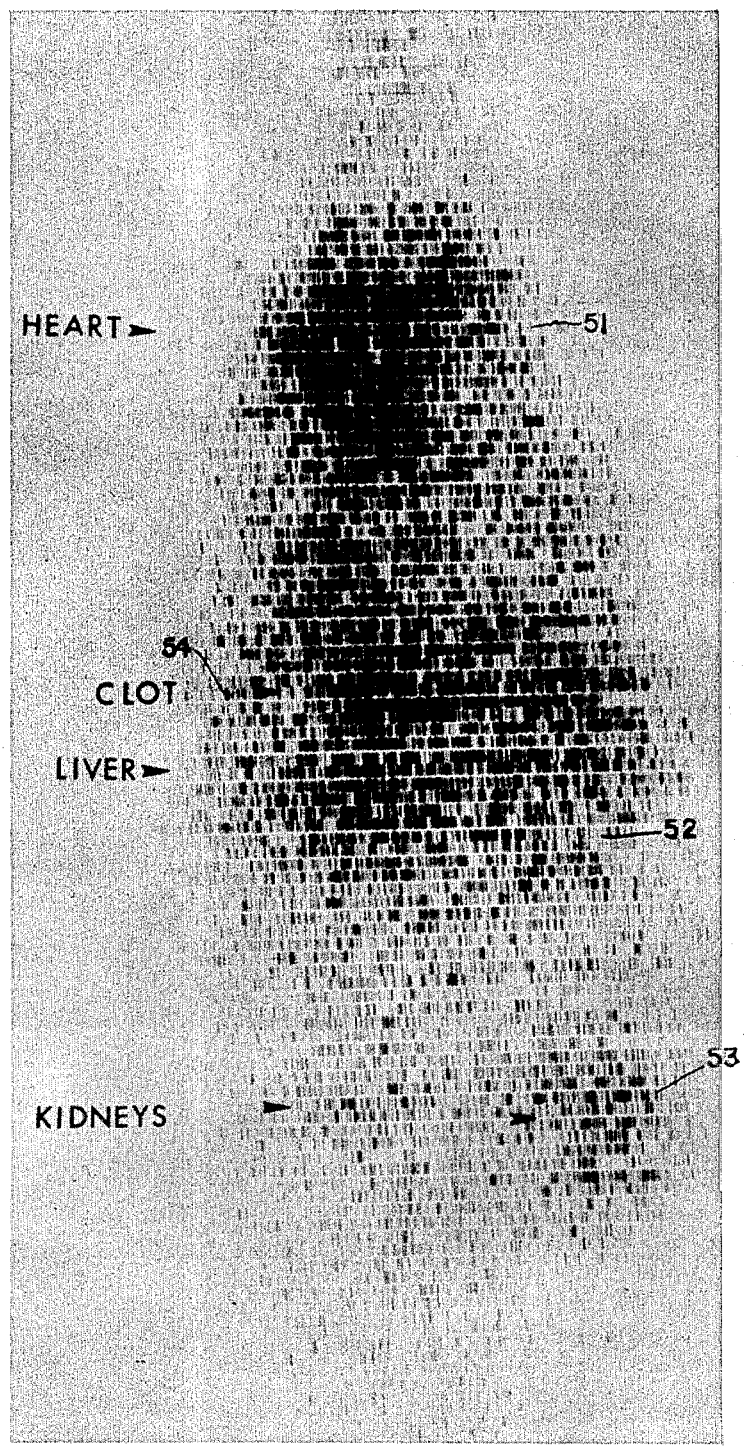
FIG. 8 is a trunk scan which depicts localization of a blood clot in the trunk of the body using the present invention.

FIG. 8 illustrates a scan made in the abdominal cavity after distribution of one of the present radionuclide-labeled enzyme in the body. Areas of the scan such as those at 51, 52, and 53 correspond to areas of the body having a large supply of blood, the numbers relating respectively to the heart, liver, and kidneys. With the passage of time after injection of the labeled enzyme into the body, any clots, such as the one indicated at 54, absorbs an increasing amount of the enzyme while the organs indicated above contain less radioactivity due to passage of the enzyme from the body or localization thereof in a clot. Thus, the area 54 corresponding to a blood clot darkens considerably with the passage of time and indicates the presence of a blood clot associated with thromboembolic disease.

The present radionuclide-labeled enzymes exhibit the chemical and enzymatic activities of the parent compounds while allowing for the first time the specific localization of blood clots associated with thromboembolic disease. Although primarily intended for the new use described hereinabove, a second potential application of the present compounds lies in the early detection of tissue rejection associated with kidney transplants. The transit time of the present compounds through the kidneys will be significantly delayed very early in the tissue rejection process, thereby allowing treatment for tissue rejection at a very early stage in the rejection process.

It is to be noted that $^{99m}Tc$-streptokinase can be used for scanning to detect blood clots. It has the same potential use as $^{99m}Tc$-urokinase. Other agents in this family of radiopharmaceuticals are listed in the table below and they all have the same use:

$^{99m}Tc$-urokinase
$^{123}I$-urokinase
$^{131}I$-urokinase
$^{99m}$-Tc-streptokinase
$^{123}I$-streptokinase
$^{131}I$-streptokinase.

Also, in addition to the above, an additional enzyme (or family of enzymes) which have a biological activity similar to urokinase and streptokinase have been purified. This enzyme is labeled with technetium-99m, iodine-123 or iodine-131 as described in this invention and can be used as radiopharmaceuticals for detecting thromboembolic disease. This enzyme is called: Tissue Plasminogen Activator (also called fibrinokinase, cytofibrinokinase, cytokinase) and a basic description of this enzyme is found in "Methods in Enzymology" 19: 821-838 (1970). Thorsen et al in "Differences in the Binding to Fibrin of Urokinase and Tissue Plasminogen Activator" Thrombos. Diathes haemorrh. (Stuttg.) 28: 65-74 (1972) present evidence which viewed in light of the findings discussed in this application suggest that tissue Plasminogen activator labeled with Technetium-99m would probably be much superior to the previously described radiopharmaceuticals.

Obviously many modifications and variations of the present invention are possible in light of the above teachings, it is, therefore, to be understood that within the scope of the appended claims the invention may be practiced otherwise than as specifically described.

What is claimed is:

1. A process for preparing a radioactive enzymatic compound consisting of urokinase and technetium-99m comprising:
   preparing a saline solution containing technetium-99m ions;
   reducing the technetium-99m ions contained in said solution by the addition of $FeCl_3$ in an acidic solution;
   adding ascorbic acid to the solution;
   adjusting the pH of the solution to a basic condition;
   adding urokinase to the solution;
   adjusting the pH of the solution to an acidic condition; and,
   separating the technetium-99m labeled urokinase from the solution.

2. The process of claim 1 wherein the technetium-99m ions are reduced by the addition of $FeCl_3$ in an aqueous solution made acid by hydrochloric acid.

3. The process of claim 2 wherein the pH of the solution is adjusted to basic conditions with the addition of sodium hydroxide and subsequently adjusted to acidic conditions by the addition of hydrochloric acid.

4. The process of claim 1 the pH of the solution is adjusted to between 7.5 and 8.5 after the addition of ascorbic acid to the solution.

5. The process of claim 4 wherein the pH of the solution is adjusted to between 5.0 and 5.5 and allowed to stand at least fifteen minutes after the addition of urokinase to the solution.

6. The process of claim 1 wherein the radioactive enzymatic compound is separated from solution by precipitation thereof from said solution by the addition of ammonium sulfate to the solution.

7. A process of specifically detecting and localizing thromboembolic disorders in the human body which comprises introducing into the bloodstream a non-lethal amount of a radiopharmaceutical sufficient to be detectable with known scanning techniques, the radiopharmaceutical being selected from the group consisting of $^{99m}$Tc-urokinase, $^{123}$I-urokinase, $^{131}$I-urokinase, $^{99m}$Tc-fibrinokinase, $^{131}$I-fibrinokinase, and $^{123}$I-fibrinokinase.

8. A radiopharmaceutical for specifically detecting and localizing thromboembolic disorders formed of an enzymatic protein capable of lysing a thromboembolism in vivo, which protein has been reacted in basic solution with a radionuclide, the solution then being acidified to remove the radiopharmaceutical, the enzymatic protein being selected from the group consisting of urokinase and fibrinokinase.

9. The radiopharmaceutical of claim 18 wherein the radionuclide is selected from the group consisting of technetium-99m, $^{131}$I, and $^{123}$I.

10. A method for localizing blood clots within the circulatory system of an organism which comprises intravenously administering an effective amount of radiopharmaceutical which is absorbed with specificity by a blood clot, the radiopharmaceutical comprising an enzyme combined with a radionuclide, the enzyme being selected from the group consisting of urokinase and fibrinokinase and the radionuclide being selected from the group consisting of technetium-99m, iodine-123, and iodine-131.

11. A radiopharmaceutical for specifically detecting and localizing thromboembolic disorders which is selected from the group consisting of $^{99}$Tc-urokinase, $^{123}$I-urokinase, $^{131}$I-urokinase, $^{99}$Tc-fibrinokinase, $^{131}$I-fibrinokinase, and $^{123}$I-fibrinokinase.

12. The radio labeled thrombolytic enzyme $^{99m}$Tc-Urokinase.

13. $^{99m}$Tc-Urokinase, being a compound of claim 12 having an activity of between 1 and 5 mCi per 20,000-100,000 CTU of Urokinase.

14. A method of detecting thromboembolisms in a vascular system which comprises introducing into said vascular system under examination an effective amount of a physiologically acceptable solution of $^{99m}$Tc labeled Urokinase and scanning said vascular system to determine the point of increased gamma radiation.

* * * * *

UNITED STATES PATENT AND TRADEMARK OFFICE
CERTIFICATE OF CORRECTION

PATENT NO. : 4,416,865

DATED : November 22, 1983

INVENTOR(S) : Buck Austin Rhodes, et al.

It is certified that error appears in the above-identified patent and that said Letters Patent are hereby corrected as shown below:

Col. 3, line 13, "alung" should read --a lung--.

Signed and Sealed this

Ninth Day of October 1984

[SEAL]

Attest:

GERALD J. MOSSINGHOFF

Attesting Officer

Commissioner of Patents and Trademarks